(12) United States Patent
Akiba et al.

(10) Patent No.: US 6,218,548 B1
(45) Date of Patent: Apr. 17, 2001

(54) PRODUCTION PROCESS OF CYCLIC COMPOUND

(75) Inventors: Toshifumi Akiba; Tutomu Ebata; Tatsuru Saito; Sadahiro Shimizu; Keiichi Hirai; Naoki Ohta; Toshiaki Tojo, all of Tokyo (JP)

(73) Assignee: Daiichi Paharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/447,831

(22) Filed: Nov. 23, 1999

Related U.S. Application Data

(62) Division of application No. 08/952,930, filed as application No. PCT/JP96/01373 on May 23, 1996, now Pat. No. 5,856,518.

(30) Foreign Application Priority Data

May 26, 1995 (JP) .................................................. 7-127756
Nov. 27, 1995 (JP) .................................................. 7-307913

(51) Int. Cl.[7] .............................................. C07D 209/54
(52) U.S. Cl. .............................................. 548/408
(58) Field of Search .............................................. 548/408

(56) References Cited

U.S. PATENT DOCUMENTS 4,228,179 * 10/1980 Hartenstein et al. ................ 424/274

FOREIGN PATENT DOCUMENTS

| 05296688 | 3/1993  | (EP) . |           |
|----------|---------|--------|-----------|
| 4149174  | 5/1992  | (JP)   | C07D/209/54 |
| 4342564  | 11/1992 | (JP)   | C07D/207/14 |
| 4342565  | 11/1992 | (JP)   | C07D/207/14 |
| 7224033  | 8/1995  | (JP)   | C07D/209/54 |
| 7233146  | 9/1995  | (JP)   | C07D/207/14 |
| 7285934  | 10/1995 | (JP)   | C07D/209/54 |
| 8157455  | 6/1996  | (JP)   | C07D/209/54 |

OTHER PUBLICATIONS

Latent Inhibitors Part 11. The Synthesis of 5–Spriocyclopropyl Dihydroorotic Acid, *Tetrahedron*, vol. 51, No. 3. pp. 865–870 1995, Stephen Husbanda et al.

J. Chem. Soc., Chem. Commun., (3) (1985), p. 119–120, Okano, Kohji et al.

* cited by examiner

Primary Examiner—Floyd D. Higel
Assistant Examiner—Ebenezer Sackey
(74) Attorney, Agent, or Firm—Sughrue, Mion, Zinn, Macpeak & Seas, PLLC

(57) ABSTRACT

A compound represented by formula (III):

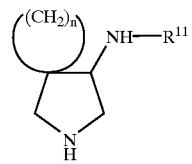

(III)

wherein n is an integer of 2 to 5; and $R^{11}$ represents a substituent group represented by formula:

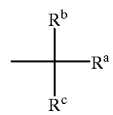

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are different from one another, and a salt thereof.

2 Claims, No Drawings

PRODUCTION PROCESS OF CYCLIC COMPOUND

This is a divisional of U.S. application No. 08/952,930 filed Nov. 26, 1997, now U.S. Pat. No. 5,856,518 the disclosure of which is incorporated herein by reference, which is a 371 of PCT/JP96/01373 filed on May 23, 1996.

TECHNICAL FIELD

This invention relates to a novel process for the synthesis of material compounds to be used in the production of a quinolone derivative which is expected as an excellent antibacterial agent (JP-A-2-231475; the term "JP-A" as used herein means an "unexamined published Japanese patent application") and to an intermediate compound useful for the production.

BACKGROUND ART

The aforementioned compound represented by formula (VI):

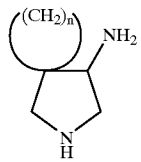

(VI)

(wherein n is an integer of 2 to 5) has been produced via a multi-step production process using ethyl acetoacetate as the starting material (JP-A-2-231475). In addition, an optically active form of this compound is obtained by preparing a diastereomer compound having an optically active protecting group, isolating it using a preparative high performance liquid chromatography and then removing the protecting group (JP-A-3-95176). However, such a method requires complex handling, hence leaving room for the improvement as an industrial production process.

It is accordingly an object of the present invention to provide a process for the inexpensive, short-step and industrially advantageous production of nitrogen-containing heterocyclic compounds having a spiro-cyclic structure, particularly an optically active azaspiro[2.4]heptane derivative.

DISCLOSURE OF INVENTION

Taking the aforementioned circumstances into consideration, the inventors of the present invention have conducted intensive studies and found that a compound of formula (I)

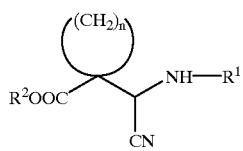

(I)

can be obtained from a known compound of formula (IV)

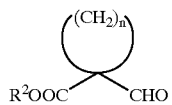

(IV)

easily with a high yield, and that the compound of formula (I) obtained therefrom can be converted easily into a compound of the following formula (II).

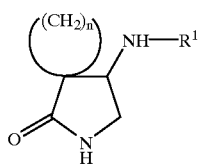

(II)

The present invention has been accomplished on the basis of such findings.

The present inventors have also found a method by which the intended compound of formula (VI):

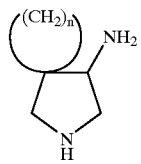

(VI)

can be obtained easily from a compound of formula (III-1):

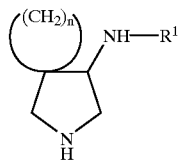

(III-1)

which is obtained by reducing the compound of formula (II).

Also, the present inventors have found that, when the compound (IV) is allowed to react with hydrogen cyanide in the presence of an optically single amine or a salt thereof, one of the thus formed two diastereomers is obtained on a preferential basis.

The present inventors have found also that one of the two diastereomers obtained above is easily epimerized when treated in a protic solvent, so that a mixture of two diastereomers can be obtained.

Accordingly, the present invention relates to a compound represented by formula (I):

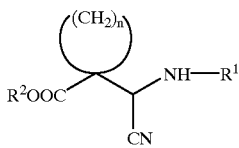

(I)

wherein
n is an integer of 2 to 5;
$R^1$ represents a hydrogen atom or a substituent group represented by formula:

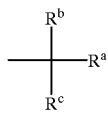

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms; and
$R^2$ represents a hydrogen atom or an alkyl group having 1 to 4 carbon atoms, with the proviso that a compound, in which n is 2, $R^1$ is hydrogen atom and $R^2$ is an ethyl group, is excluded, and a salt thereof.

The present invention also relates to a compound represented by formula (II):

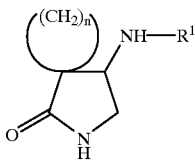

(II)

wherein
n is an integer of 2 to 5; and
$R^1$ represents a hydrogen atom or a substituent group represented by formula:

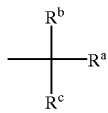

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, and a salt thereof.

The present invention also relates to a compound represented by formula (III):

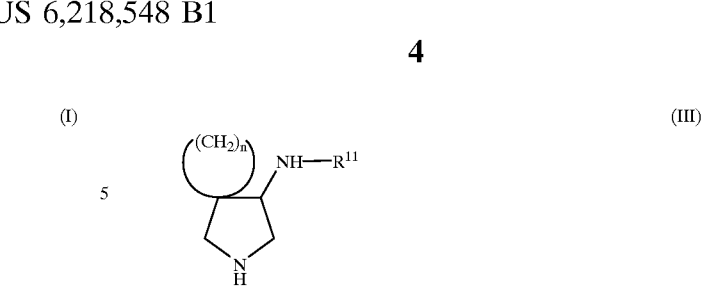

(III)

wherein
n is an integer of 2 to 5; and
$R^{11}$ represents a substituent group represented by formula:

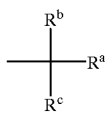

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are different from one another, and a salt thereof.

The present invention also relates to a process for the production of a compound represented by formula (I):

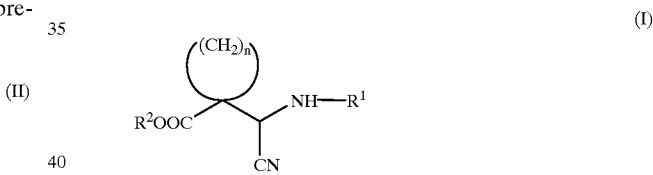

(I)

wherein
n is an integer of 2 to 5;
$R^1$ represents a hydrogen atom or a substituent group represented by formula:

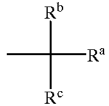

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time; and
$R^2$ represent a hydrogen atom or an alkyl group having 1 to 4 carbon atoms,
which comprises allowing a compound represented by formula (IV):

which comprises reducing the cyano group of a compound represented by formula (I):

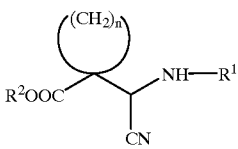

(I)

wherein
n is an integer of 2 to 5;
$R^1$ represents a hydrogen atom or a substituent group represented by formula:

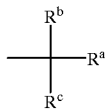

wherein
$R^a$, $R^b$ and $R^c$ each represents a phenyl, phenylmethyl or naphthyl group (which may be substituted with at least: one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms; and
$R^2$ represents a hydrogen atom or an alkyl group having 1 to 4 carbon atoms, and subsequently effecting cyclization of the resulting amino compound.

The present invention also relates to a process for the production of a compound represented by formula (III-1):

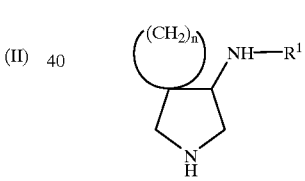

(III-1)

wherein
n is an integer of 2 to 5; and
$R^1$ represents a hydrogen atom or a substituent group represented by formula:

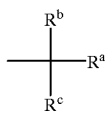

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms,
which comprises reducing the just described compound of formula (II).

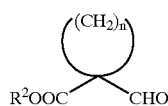

(IV)

wherein
n is an integer of 2 to 5 and $R^2$ represents a hydrogen atom or an alkyl group having 1 to 4 carbon atoms, to react with hydrogen cyanide in the presence of a compound represented by the following formula (V) or a salt thereof:

$NH_2R^1$ (V)

wherein
$R^1$ represents a hydrogen atom or a substituent group represented by formula:

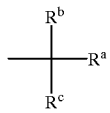

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time.

The present invention also relates to a process for the production of a compound represented by formula (II):

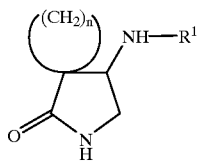

(II)

wherein
n is an integer of 2 to 5; and
$R^1$ represents a hydrogen atom or a substituent group represented by formula:

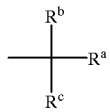

wherein
$R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, The present invention also relates to a process for the preparation of a compound represented by formula (VI):

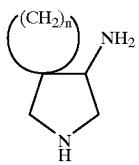
(VI)

wherein n is an integer of 2 to 5, which comprises removing the substituent group $R^{12}$ of a compound of formula (III-2):

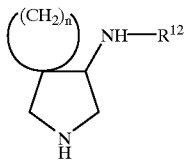
(III-2)

wherein n is an integer of 2 to 5; and $R^{12}$ represents a substituent group represented by formula:

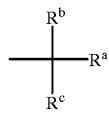

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms.

The present invention also relates to a process for the production of a compound represented by the following formula (I):

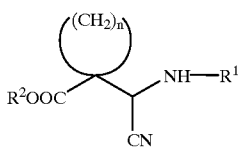
(I)

wherein n is an integer of 2 to 5;

$R^1$ represents a hydrogen atom or a substituent group represented by formula:

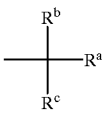

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time; and $R^2$ represents a hydrogen atom or an alkyl group having 1 to 4 carbon atoms, in a diastereo-selective manner, namely a process in which one of its two diastereomers is obtained on a preferential basis, which comprises allowing a compound represented by formula (IV):

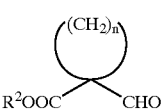
(IV)

wherein n is an integer of 2 to 5 and $R^2$ represents a hydrogen atom or an alkyl group having 1 to 4 carbon atoms to react with hydrogen cyanide in the presence of an optically single form of a compound represented by the following formula (V) or a salt thereof:

$$NH_2R^1 \qquad (V)$$

wherein $R^1$ represents a hydrogen atom or a substituent group represented by formula:

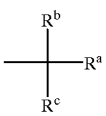

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time.

The present invention also relates to a process for the production of a diastereomer mixture of a compound represented by formula (I-1):

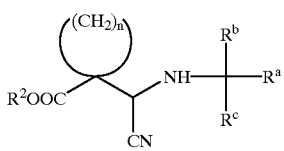

(I-1)

wherein n is an integer of 2 to 5; $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time; and $R^2$ represents a hydrogen atom or an alkyl group having 1 to 4 carbon atoms, which comprises treating an optically single compound of the compound of formula (I-1) in a protic solvent to effect the isomerization thereof.

The present invention will be described hereinafter in detail.

The term "optically single compound" as used herein means that it is comprised of any one of a plurality of optical isomers when they are present, and it includes not only a compound completely free from other optical isomers but also a compound having a chemically pure degree. In other words, it may contain other optical isomers, provided that they do not exert influences upon its physical constants and physiological activity.

Firstly, the compound of the present invention represented by formula (I):

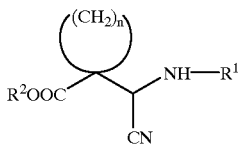

(I)

is described. In this formula, n is an integer of 2 to 5, and the substituent group $R^1$ is a hydrogen atom or a substituent group represented by formula:

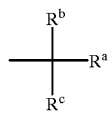

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms.

When the substituent group $R^1$ is a substituent group represented by formula:

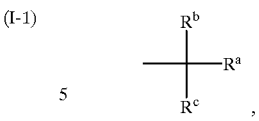

it may be any group which is not changed by the reaction to convert the cyano group of the compound of formula (I) into aminomethyl group, but preferably a group in which $R^a$, $R^b$ and $R^c$ are different from one another. Illustrative examples of such a case include (R)- and (S)-1-phenylethyl, (R)- and (S)-1-phenylpropyl, (R)- and (S)-1-phenyl-2-(p-tolyl)ethyl, (R)- and (S)-1-(1-naphthyl)ethyl and the like groups.

Of these groups, (R)- or (S)-1-phenylethyl group is preferred in view of simple and easy production, and its phenyl group may have another substituent groups. For example, it may have at least one substituent group selected from the group consisting of an alkyl group having 1 to 4 carbon atoms, an alkoxyl group having 1 to 4 carbon atoms, a halogen atom and a nitro group. Illustrative examples of such groups include (R)- and (S)-1-(4-methoxyphenyl)ethyl, (R)- and (S)-1-(4-chlorophenyl)ethyl, (R)- and (S)-1-(4-nitrophenyl)ethyl, (R)- and (S)-1-(2,4-dichlorophenyl)ethyl, (R)- and (S)-1-(2,4-dinitrophenyl)ethyl, (R)- and (S)-1-(3,5-dichlorophenyl)ethyl, (R)- and (S)-1-(3,5-dinitrophenyl)ethyl and the like groups.

The substituent group $R^1$ may be an amino group-protecting group. In such case, $R^1$ may be a protecting group which is not changed by the reaction to convert the cyano group of the compound of formula (I) into aminomethyl group. Illustrative examples of such amino group-protecting groups include alkoxycarbonyl groups such as tert-butoxycarbonyl, 2,2,2-trichloroethoxycarbonyl and the like groups, aralkyloxycarbonyl groups such as benzyloxycarbonyl, p-methoxybenzyloxycarbonyl, p-nitrobenzyloxycarbonyl and the like groups, aliphatic or aromatic acyl groups such as acetyl, methoxyacetyl, trifluoroacetyl, chloroacetyl, pivaloyl, formyl, benzoyl and the like groups and aralkyl groups such as benzyl, p-nitrobenzyl, p-methoxybenzyl, triphenylmethyl and the like groups.

Of these protecting groups, aralkyl groups are preferred in view of simple and easy production. Of these aralkyl groups, benzyl group is preferred. The phenyl group of the benzyl group may have another substituent groups. For example, it may have at least one substituent group selected from the group consisting of an alkyl group having 1 to 4 carbon atoms, an alkoxyl group having 1 to 4 carbon atoms, a halogen atom and a nitro group. Illustrative examples of such groups other than benzyl group include 4-methoxybenzyl, 4-chlorobenzyl, 4-nitrobenzyl, 2,4-dichlorobenzyl, 2,4-dinitrobenzyl, 3,5-dichlorobenzyl, 3,5-dinitrobenzyl and the like groups.

The substituent group $R^2$ represents a hydrogen atom or an alkyl group having 1 to 4 carbon atoms, but the "alkyl group" may be a straight- or branched chain alkyl group. Further, the substituent group $R^2$ is not always limited to such an alkyl group, provided that it functions as a elimination group.

Next, the compound of the present invention represented by formula (II):

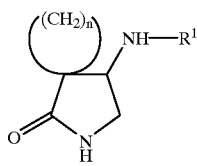
(II)

is described. In this formula, n is an integer of 2 to 5, and the substituent group $R^1$ is hydrogen atom or a substituent group represented by formula:

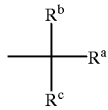

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms.

As the substituent group of the following formula,

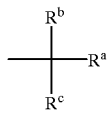

the same substituent groups described in relation to the compound of formula (I) may be used. Further, the substitutent group $R^1$ may be an amino group-protecting group as in the compound of formula (I):

Next, the compound of the present invention represented by formula (III):

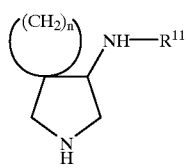
(III)

is described. In this formula, n is an integer of 2 to 5, and the substituent group $R^{11}$ is a substituent group represented by formula:

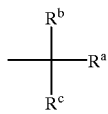

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are different from one another.

Illustrative examples of the substituent group represented by formula:

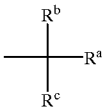

include (R)- and (S)-1-phenylethyl, (R)- and (S)-1-phenylpropyl, (R)- and (S)-1-phenyl-2-(p-tolyl)ethyl, (R)- and (S)-1-(1-naphthyl)ethyl and the like groups.

Of these groups, (R)- or (S)-1-phenylethyl group is preferred in view of simple and easy production, and its phenyl group may have another substituent groups. For example, it may have at least one substituent group selected from the group consisting of an alkyl group having 1 to 4 carbon atoms, an alkoxyl group having 1 to 4 carbon atoms, a halogen atom and a nitro group. Illustrative examples of such groups include (R)- and (S)-1-(4-methoxyphenyl)ethyl, (R)- and (S)-1-(4-chlorophenyl)ethyl, (R)- and (S)-1-(4-nitrophenyl)ethyl, (R)- and (S)-1-(2,4-dichlorophenyl)ethyl, (R)- and (S)-1-(2,4-dinitrophenyl)ethyl, (R)- and (S)-1-(3,5-dichlorophenyl)ethyl, (R)- and (S)-1-(3,5-dinitrophenyl)ethyl and the like groups.

Next, production process of the compounds of the present invention, firstly the compound represented by formula (I),

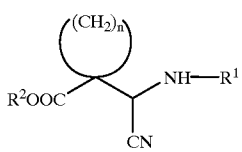
(I)

is described.

According to the present invention, a compound represented by the following formula (IV-2) is used for the synthesis of one of the compound of formula (I) in which n is 2, and this starting compound can be synthesized by a known method. For example, it can be obtained from 1-cyano-cyclopropanecarbonic acid ester in accordance with the following reaction scheme when the method of Meyers et al. (*J. Org. Chem.*, 1973, 38, 36) is employed.

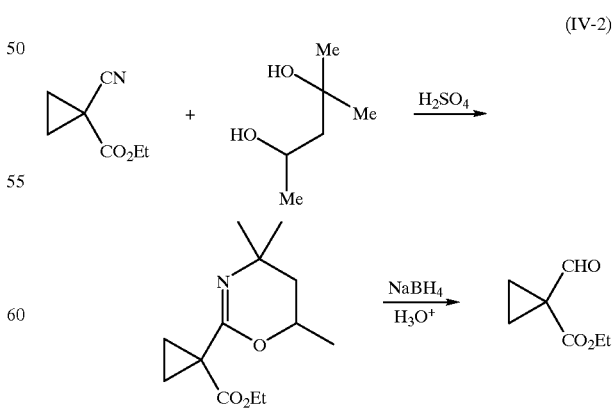
(IV-2)

Production of the compound of formula (I) from the compound of formula (IV) can be effected by allowing the compound of formula (IV) to react with hydrogen cyanide in the presence of a compound represented by the following formula (V) or a salt thereof:

$$NH_2R^1 \quad (V)$$

wherein $R^1$ represents a hydrogen atom or a substituent group represented by formula:

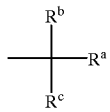

wherein $R^a$, $R^b$ and $R^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that $R^a$, $R^b$ and $R^c$ are not hydrogen atoms at the same time.

Examples of the salt of this case include acid addition salts such as hydrochloride, hydrobromide, nitrate and the like inorganic acid salts.

Each of $R^a$, $R^b$ and $R^c$ is a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, and $R^a$, $R^b$ and $R^c$ may preferably be different from one another. That is, a compound having asymmetric carbon is preferred as the compound of formula (V). More preferred is a case of either of the two optical isomers, namely optically single compound.

Illustrative examples of the compound of formula (V) include (R)- and (S)-1-phenylethylamine, (R)- and (S)-1-phenylpropylamine, (R)- and (S)-1-phenyl-2-(p-tolyl)ethylamine, (R)- and (S)-1-(1-naphthyl)ethylamine, (R)- and (S)-1-(4-methoxyphenyl)ethylamine, (R)- and (S)-1-(4-chlorophenyl)ethylamine, (R)- and (S)-1-(4-nitrophenyl)ethylamine, (R)- and (S)-1-(2,4-dichlorophenyl)ethylamine, (R)- and (S)-1-(2,4-dinitrophenyl)ethylamine, (R)- and (S)-1-(3,5-dichlorophenyl)ethylamine, (R)- and (S)-1-(3,5-dinitrophenyl)ethylamine and the like.

Hydrogen cyanide to be used in this reaction may be generated outside the reaction system and introduced into the system or directly generated in the reaction system. Its generation in the reaction system may be effected by employing a salt exchange reaction of potassium cyanide, sodium cyanide, lithium cyanide and the like alkali cyanides with various acidic substances, typically hydrochloric acid, in water. Alternatively, it may be generated by adding sodium hydrogen sulfite or the like reducing agent to the just described alkali cyanides. In this connection, trimethylsilyl cyanide or the like organic cyanide or diethylaluminum cyanide or the like organic metal cyanide may be used in stead of hydrogen cyanide.

Any solvent can be used in this reaction, provided that it is inert to the reaction, preferably water or a solvent which is miscible with water. Examples of the water-miscible solvent include alcohols such as methanol, ethanol, propanol, isopropanol and the like, ethers such as tetrahydrofuran, dioxane and the like, ketones such as acetone and the like and nitrogen-containing solvents such as acetonitrile and the like. As occasion demands, these solvents may be used as water-containing solvents.

This reaction is carried out at a temperature of approximately from −20 to 100° C., preferably from 50° C. to the boiling point of solvent used.

When this reaction is carried out with an optically single amine, the product becomes a mixture of two diastereomers, but one of the diastereomers is formed preferentially than the other. In other words, this reaction is characterized by the diastereo-selective reaction. For example, when (S)-1-phenylethylamine is used as the amine, the product becomes a mixture of 1-[(S)-1-cyano-[(S)-1-phenylethylamino]methyl]-1-ethoxycarbonylcyclopropane and its diastereomer 1-[(R)-1-cyano-[(S)-1-phenylethylamino]methyl]-1-ethoxycarbonylcyclopropane, with a formation ratio of 73:27. In this connection, when (R)-1-phenylethylamine is used, the product becomes a mixture of 1-[(S)-1-cyano-[(R)-1-phenylethylamino]methyl]-1-ethoxycarbonylcyclopropane and its diastereomer 1-[(R)-1-cyano-[(R)-1-phenylethylamino]methyl]-1-ethoxycarbonylcyclopropane, and the formation ratio will become about 3:7.

The thus obtained two diastereomers can be separated by usually used means, such as silica gel column chromatography, thin layer chromatography, high performance liquid chromatography and the like.

Of the thus separated optical isomers, an isomer which is not necessary can be converted into a diastereomer mixture containing necessary isomer by treating it in a protic solvent to effect epimerization easily, i.e., converting the configuration of the carbon atom bonded to a cyano group. Then, the compound having the desired configuration can be separated from the mixture.

Such a treatment may be carried out with heating. Any ptotic solvent can be used, provided that it is inert to the compound, with its preferred examples including methanol, ethanol, propanol, isopropanol and the like alcohols. Mixture solvents of these protic solvents with other solvents may also be used. Examples of such other solvents include ethers such as tetrahydrofuran and the like, ketones such as acetone and the like, nitrogen-containing solvents such as acetonitrile and the like, aromatic hydrocarbon solvents such as toluene and the like and aliphatic hydrocarbon solvents such as hexane and the like. That is, when the 1-[(R)-1-cyano-[(S)-1-phenylethylamino]methyl]-1-ethoxycarbonylcyclopropane obtained above is heated under reflux for 30 minutes in ethanol, it becomes a 73:27 mixture of 1-[(S)-1-cyano-[(S)-1-phenylethylamino]methyl]-1-ethoxycarbonylcyclopropane and 1-[(R)-1-cyano-[(S)-1-phenylethylamino]methyl]-1-ethoxycarbonylcyclopropane. Thus, it is possible to introduce it easily into an optically active form having either one of the configurations.

In this connection, a member of the compound of formula (I) in which the substituent group $R^1$ is an alkoxycarbonyl group, an aralkyloxycarbonyl group or an aliphatic or aromatic acyl group can be obtained easily by converting it from a compound of formula (I) whose $R^1$ is a hydrogen atom by means of usually used substitution reaction.

Next, a process for the production of the compound of formula (II) from the compound of formula (I) is described.

The compound of formula (II) can be produced by reducing the cyano group of the compound of formula (I) and then effecting cyclization of the thus formed amino compound. The reduction and cyclization can be effected by reducing the starting compound in an atmosphere of hydrogen in the presence of a catalyst and then carrying out condensation cyclization continuously with heating. Alternatively, the amino compound of the following formula obtained by the reduction reaction

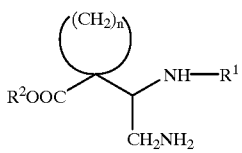

may be once isolated and then heated to effect cyclization. Any reaction can be used in this reaction, provided that it is inert to ester and $R^1$ and can reduce the cyano group into aminomethyl group. Examples of such a reaction include a catalytic hydrogenation reaction which uses palladium-carbon, Raney nickel and the like catalysts, of which a reaction in which Raney nickel is used is particularly preferred.

Any solvent can be used in this reaction, provided that it is inert to the reaction. Preferred examples of the solvent include methanol, ethanol, propanol, isopropanol and the like alcohols and 1,4-dioxane and the like ethers. These solvents may be used by dissolving ammonia therein. As occasion demands, these solvents may be used by mixing with water. The ammonia-containing solvent may be prepared by dissolving ammonia gas in a solvent or mixing it with aqueous ammonia.

The catalytic hydrogenation reaction is carried out at a temperature of approximately from 0 to 40° C., preferably from 5 to room temperature. The cyclization reaction is carried out at a temperature of approximately from 0 to 200° C., preferably from room temperature to 180° C. The hydrogen gas pressure at the time of the catalytic hydrogenation may be within the range of from 1 to 100 atmospheric pressures, preferably from 20 to 70 atmospheric pressures. When the catalytic hydrogenation reaction is carried out approximately at room temperature, it may sometimes be necessary to carry out the cyclization reaction by continuously heating the reaction system at from 50° C. to 180° C.

Next, a process for the production of the compound of formula (III-1) from the compound of formula (II) is described.

The compound of formula (III-1) can be produced by reducing the compound of formula (II). In general, the carbonyl moiety of the amide group is reduced by allowing a hydrogenation agent to react therewith. Examples of the hydrogenation agent to be used in this reaction include aluminum hydride compounds such as lithium aluminum hydride, sodium aluminum bis(2-methoxyethoxy)hydride and the like and various boron compounds (diborane and the like for instance) which are used in the combination system of sodium borohydride with methanesulfonic acid, boron trifluoride and the like, of which lithium aluminum hydride and sodium aluminum bis(2-methoxyethoxy)hydride are particularly preferred.

This reaction is generally carried out in the presence of a solvent which is not particularly limited with the proviso that it is inert to the reaction. Examples of the solvent include diethyl ether, tetrahydrofuran and the like ethers and toluene and the like hydrocarbon solvents, of which tetrahydrofuran is preferred.

This reaction may be carried out at a temperature of from 0° C. to the boiling point of used solvent, preferably from room temperature to 100° C.

Next, a process for the production of the compound of formula (VI) from the compound of formula (III-2) is described.

The compound of formula (VI) can be produced by removing $R^{12}$ from the compound of formula (III-2) by its catalytic hydrogenation or acid hydrolysis.

For example, when a catalytic hydrogeneration is employed, palladium-carbon, palladium hydroxide, Raney nickel and the like may be used as the catalyst, of which palladium-carbon and palladium hydroxide are particularly preferred. Any solvent can be used in this reaction, provided that it is inert to the reaction. Preferred examples of the solvent include methanol, ethanol, propanol, isopropanol and the like alcohols and tetrahydrofuran and the like ethers. These solvents may be used by adding water. As occasion demands, these solvents may be used by adding acetic acid, hydrochloric acid or the like acid.

This reaction is carried out at a temperature of from 0 to 100° C., preferably from 5 to 50° C. The hydrogen gas pressure of this reaction may be within the range of from 1 to 100 atmospheric pressures, preferably from 1 to 50 atmospheric pressures.

The aforementioned processes can be summarized as follows (for example, the case wherein $R^2$ is an ethyl group).

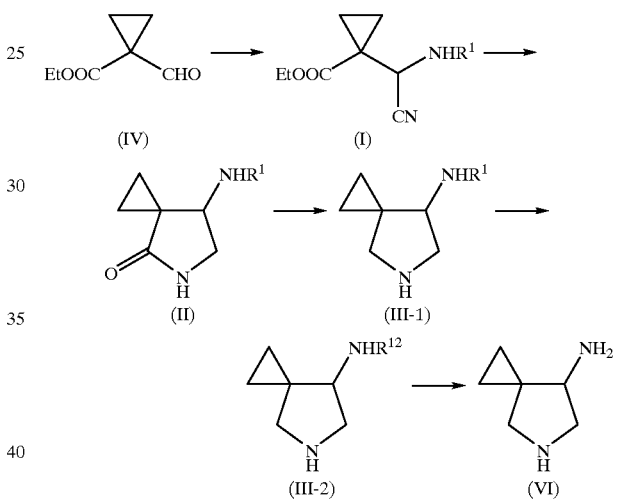

Optically active form (antipode) of the compound represented by formula (VI):

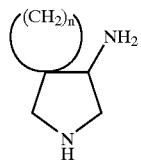

can be produced in the following manner (for example, the case wherein $R^2$ is ethyl group, $R^a$ is a methyl group, $R^b$ is a phenyl group and $R^c$ is a hydrogen atom).

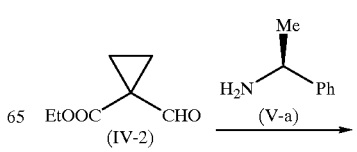

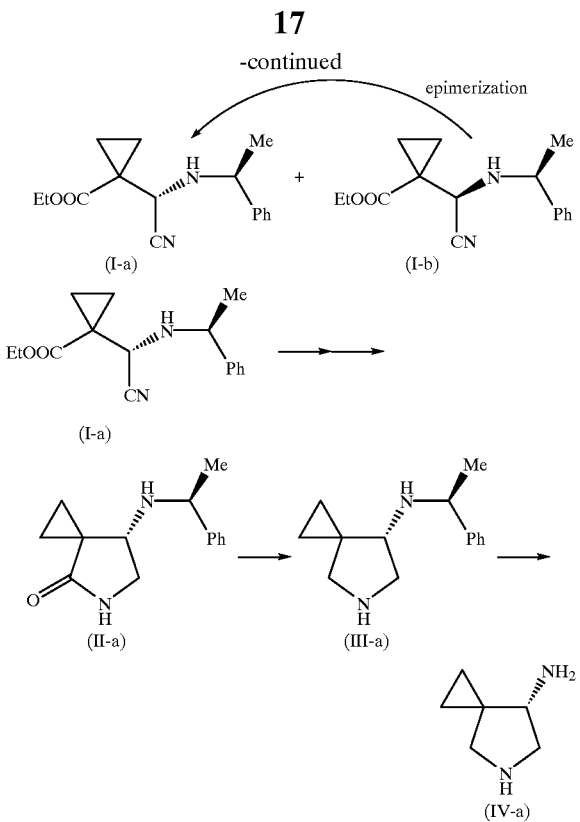

That is, the compound of formula (I) is produced by allowing the compound of formula (IV) to react with hydrogen cyanide in the presence of an optically single compound of the compound of formula (V) or a salt thereof. The term "optically single compound of the compound of formula (V)" means either of two optical isomers when they exist in the compound of formula (V) in which $R^a$, $R^b$ and $R^c$ are different from one another.

When this reaction is carried out with an optically single amine as shown above, the compound of formula (I) is formed as a mixture of two diastereomers, but a diastereoselective reaction progresses and one of the diastereomers is formed preferentially than the other. The thus obtained two diastereomers can be separated by usually used means to obtain only the necessary optical isomer. In this connection, one of the thus obtained optically active isomers, which is not necessary, can be converted easily into necessary isomer by effecting epimerization in a protic solvent, i.e., converting the configuration of the carbon atom bonded to a cyano group, so that it is possible to obtain only an optically active substance having either one of the configurations.

Next, the compound of formula (II) is obtained as an optically single compound by reducing the cyano group of the thus obtained optically single compound of formula (I) and then effecting cyclization of the thus formed amino compound.

Next, the compound of formula (III-1) is obtained as an optically single compound by reducing the thus obtained optically single compound of formula (II).

Finally, the compound of formula (VI) is produced as an optically single compound by subjecting the optically single compound of formula (III-2) to catalytic hydrogenation or acid hydrolysis to effect the deprotection.

Alternatively, an optically active form (antipode) of the compound of formula (VI) can also be produced by forming diastereomer salts of a racemate of the compound represented by formula (VI) with an optically active acid such as tartaric acid and subsequently carrying out optical resolution. Since the compound of formula (VI) is a dibasic compound, two diastereomer salts [compound (VI):tartaric acid=1:1 and compound (VI):tartaric acid=1:2] are obtained which can be produced selectively. For example, (S)-form of the compound of formula (VI) can be produced by forming its 1:1 salt with D-tartaric acid, and isolating the salt by recrystallization to carry out optical resolution. Examples of the preferred solvent to be used in this case include methanol, ethanol and the like alcohol solvents which may be used alone or as a mixture solvent with water.

The thus obtained compound of formula (VI) can be introduced into an excellent antibacterial agent in accordance with the method disclosed in JP-A-2-231475 and JP-A-3-95176.

BEST MODE FOR CARRYING OUT INVENTOIN

Examples of the present invention are given below by way of illustration and not by way of limitation.

INVENTIVE EXAMPLE 1

1-(1-Amino-1-cyanomethyl)-1-ethoxycarbonylcyclopropane

An eggplant type flask-was charged with 3.49 g of potassium cyanide and 3.74 g of ammonium chloride, and the contents were dissolved in 20 ml of water. After adding 40 ml of concentrated ammonia water to the solution, 5.01 g of ethyl 1-formylcyclopropane-1-carboxylate dissolved in 30 ml of ethanol was added thereto dropwise at room temperature, and the reaction solution was stirred for 2 hours at 50° C. After confirming completion of the reaction, the reaction solution was mixed with ice water and extracted with ethyl acetate. Next, the resulting organic layer was washed with water and saturated brine, dried over anhydrous magnesium sulfate and, after removing insoluble matter by filtration, concentrated under a reduced pressure. Thereafter, the resulting residue was subjected to a silica gel column chromatography (ethyl acetate) to obtain 5.44 g (97%) of the title compound in the form of colorless oil.

$^1$H-NMR (CDCl$_3$) δ: 1.02–1.10 (2H, m), 1.28 (3H, t, J=7.3 Hz), 1.40–1.44 (2H, m), 2.03 (2H, brs), 3.61 (1H, s), 4.21 (2H, q, J=7.3 Hz). IR (KBr) cm$^{-1}$: 2988, 1724, 1378, 1192. MS (m/z): 169, 128.

INVENTIVE EXAMPLE 2

1-(1-Benzylamino-1-cyanomethyl)-1-ethoxycarbonylcyclopropane

An eggplant type flask was charged with 131 mg of potassium cyanide and 539 mg of benzylamine, and the contents were dispersed in 1 ml of water. Thereto was added dropwise 146 mg of ethyl 1-formylcyclopropane-1-carboxylate dissolved in 2 ml of ethanol at room temperature, followed by dropwise addition of 0.2 ml of concentrated hydrochloric acid. The reaction solution was stirred for 2.5 hours at 50° C. After confirming completion of the reaction, the reaction solution was mixed with ice water and extracted with ethyl acetate. Next, the resulting organic layer was washed with saturated brine, dried over anhydrous sodium sulfate and, after removing insoluble matter by filtration, concentrated under a reduced pressure. Thereafter, the resulting residue was subjected to a silica gel column chromatography (hexane:ethyl acetate=5:1) to obtain 231 mg (87%) of the title compound in the form of colorless oil.

$^1$H-NMR (CDCl$_3$) δ: 0.93–0.97 (2H, m), 1.26 (3H, t, J=7.3 Hz), 1.39–1.42 (2H, m), 2.59 (1H, brs), 3.10 (1H, s), 3.81 (1H, d, J=13 Hz), 4.09–4.23 (3H, m), 7.25–7.39 (5H, m). IR (KBr) cm$^{-1}$: 2988, 1726, 1376, 1180. MS (m/z): 259, 232, 106, 91.

INVENTIVE EXAMPLE 3

1-(1-Benzylamino-1-cyanomethyl)-1-ethoxycarbonylcyclopropane

An eggplant type flask was charged with 501 mg of ethyl 1-formylcyclopropane-1-carboxylate and 2 ml of water to which were further added 1.13 g of sodium hydrogen sulfite and 345 mg of potassium cyanide. Thereto was added dropwise 564 mg of benzylamine dissolved in 5 ml of ethanol at room temperature, followed by 2.5 hours of stirring the reaction solution at 50° C. After confirming completion of the reaction, the reaction solution was mixed with ice water and extracted with ethyl acetate. Next, the resulting organic layer was washed with saturated brine, dried over anhydrous magnesium sulfate and, after removing insoluble matter by filtration, concentrated under a reduced pressure. Thereafter, the resulting residue was subjected to a silica gel column chromatography (hexane:ethyl acetate=3:1) to obtain 717 mg (79%) of the title compound in the form of colorless oil. Spectrum data of the thus obtained oily product coincided with those of the compound of Inventive Example 2.

INVENTIVE EXAMPLE 4

1-(1-t-Butoxycarbonylamino-1-cyanomethyl)-1-ethoxycarbonylcyclopropane

An eggplant type flask was charged with 100 mg of 1-(1-amino-1-cyanomethyl)-1-ethoxycarbonylcyclopropane which was subsequently dissolved in 1 ml of toluene. Thereto were added 300 mg of di-t-butyl dicarbonate and 0.2 ml of triethylamine while cooling in an ice bath, followed by 5 hours of stirring at room temperature. After completion of the reaction, the reaction solution was washed with saturated citric acid aqueous solution and saturated brine, dried over anhydrous sodium sulfate and, after removing insoluble matter by filtration, concentrated under a reduced pressure. Thereafter, the resulting residue was subjected to a silica gel column chromatography (hexane:ethyl acetate=5:1) to obtain 112 mg (70%) of the title compound in the form of colorless oil.

$^1$H-NMR (CDCl$_3$) δ: 1.02–1.55 (4H, m), 1.29 (3H, t, J=7.3 Hz), 1.46 (9H, s), 4.08–4.29 (3H, m), 5.78 (1H, br)

INVENTIVE EXAMPLE 5

7-Amino-4-oxo-5-azaspiro[2.4]heptane

An autoclave was charged with 1.0 g of 1-(1-amino-1-cyanomethyl)-1-ethoxycarbonylcyclopropane, 0.4 ml of Raney nickel and 4.0 ml of ammonia-saturated ethanol, and the contents were stirred at 80° C. for 4 hours in an atmosphere of hydrogen under a pressure of 20 kg/cm$^2$. After completion of the reaction, the catalyst was removed by filtration and the resulting filtrate was concentrated under a reduced pressure to obtain 692 mg (92%) of the title compound in the form of colorless crystals. The thus obtained product was recrystallized from ethyl acetate and diethyl ether and used as a sample for analyses.

Melting point: 97–99° C. $^1$H-NMR (CDCl$_3$) δ: 0.81–0.92 (2H, m), 1.01–1.13 (2H, m), 3.12 (1H, dd, J=4.3, 10.2 Hz), 3.46 (1H, dd, J=4.3, 7.3 Hz), 3.72 (1H, dd, J=7.3, 10.2 Hz). IR (KBr) cm$^{-1}$: 3328, 3208, 1682, 1026, 972. MS (m/z): 127, 110. Elemental analysis for C$_6$H$_{10}$N$_2$O: Calcd.(%); C, 57.12; H, 7.99; N, 22.21 Found (%); C, 57.00; H, 7.83; N, 22.18.

INVENTIVE EXAMPLE 6

7-Benzylamino-4-oxo-5-azaspiro[2.4]heptane

An autoclave was charged with 61.3 mg of 1-(1-benzylamino-1-cyanomethyl)-1-ethoxycarbonylcyclopropane, 0.2 ml of Raney nickel and 2.0 ml of ammonia-saturated ethanol, and the contents were stirred at room temperature for 2 hours in an atmosphere of hydrogen under a pressure of 30 kg/cm$^2$. After completion of the reaction, the catalyst was removed by filtration and the resulting filtrate was concentrated under a reduced pressure to obtain 51.3 mg (quantitative) of the title compound in the form of light yellow oil.

$^1$H-NMR (CDCl$_3$) δ: 0.74–1.28 (4H, m), 3.27 (1H, dd, J=4.0 and 9.6 Hz), 3.40 (1H, dd, J=4.0, 6.9 Hz), 3.66 (1H, dd, J=6.9, 9.6 Hz), 3.72 (1H, d, J=13.2 Hz), 3.72 (1H, d, J=13.2 Hz). IR (KBr) cm$^{-1}$: 3260, 1698, 1454, 744. MS (m/z): 217, 91, 75.

INVENTIVE EXAMPLE 7

7-t-Butoxycarbonylamino-4-oxo-5-azaspiro[2.4]heptane

An autoclave was charged with 112 mg of 1-(1-t-butoxycarbonylamino-1-cyanomethyl)-1-ethoxycarbonyl-cyclopropane, 0.5 ml of Raney nickel and 3.0 ml of ammonia-saturated ethanol, and the contents were stirred at 80° C. for 2 hours in an atmosphere of hydrogen under a pressure of 65 kg/cm$^2$. After completion of the reaction, the catalyst was removed by filtration and the resulting filtrate was concentrated under a reduced pressure to obtain 86 mg (91%) of the title compound in the form of colorless crystals. The thus obtained compound was recrystallized from ethyl acetate and diethyl ether, and used as a sample for analyses.

Melting point: 178–181° C. $^1$H-NMR (CDCl$_3$) δ: 0.9–1.3 (4H, m), 1.43 (9H, s), 3.30 (1H, brd, J=9.9 Hz), 3.80 (1H, brdd, J=7.3 and 9.9 Hz), 4.17 (1H, br), 5.03 (1H, br), 6.90 (1H, br). IR (KBr) cm$^{-1}$: 3336, 1690, 1680, 1538. MS (m/z): 227, 171, 110. Elemental analysis for C$_{11}$H$_{18}$N$_2$O$_3$: Calcd. (%); C, 58.39; H, 8.01; N, 12.38 Found (%); C, 58.22; H. 8.04; N, 12.19.

INVENTIVE EXAMPLE 8

7-Amino-5-azaspiro[2.4]heptane p-toluenesulfonate

A flask was charged with 50 mg of 7-amino-4-oxo-5-azaspiro[2.4]heptane, and the atmosphere in the flask was replaced with nitrogen. Next, 1.0 ml of tetrahydrofuran was added to dissolve the compound in the flask, 2.0 ml of lithium aluminum hydride (1 M solution in tetrahydrofuran) was added dropwise to the resulting solution at room temperature and then the mixture was heated under reflux for 7.5 hours. After confirming completion of the reaction, the reaction was terminated by adding saturated ammonium chloride aqueous solution and then the insoluble matter was removed by filtration. The resulting filtrate was concentrated under a reduced pressure to obtain 42.5 mg (95.7%) of colorless oily substance. The thus obtained oily substance was dissolved in ethanol, mixed with 2 equivalents of p-toluenesulfonic acid monohydrate. Thereafter, diethyl ether was added thereto, and the precipitated crystals were recrystallized from ethanol and diethyl ether to be used as a sample for analyses.

Melting point: 232–238° C. $^1$H-NMR (D$_2$O, H$_2$O=4.65 ppm) δ: 0.9–1.2 (4H, m), 2.34 (6H, s), 3.16 (1H, d, J=11.9 Hz), 3.15–3.74 (3H, m), 4.01 (1H, dd, J=7.6 and 13.9 Hz), 7.31 (4H, d, J=8.3 Hz), 7.63 (4H, d, J=8.3 Hz). IR (KBr) cm$^{-1}$: 2988, 1206, 1172, 1124, 682, 568. Elemental analysis for C$_{20}$H$_{28}$N$_2$O$_6$S$_2$: alcd.(%); C, 52.61; H, 6.18; N, 6.14 Found (%); C, 52.66; H, 6.19; N, 6.19.

INVENTIVE EXAMPLE 9

(S)-7-Amino-5-azasipror[2.4]heptane

A 375 mg portion of 7-amino-5-azaspiro[2.4]heptane was put into a flask, dispersed in 22.0 ml of methanol and then mixed with 1.0 g of D-tartaric acid which has been dissolved in 4.0 ml of water. The resulting solution was cooled in an ice bath while carrying out inoculation and stirred for a while and then the thus precipitated crystals were collected by filtration. By further repeating this step three times, 361 mg (38.6%) of colorless prism crystals were obtained.

Meltng point: 158–163° C. $^1$H-NMR (D$_2$O, H$_2$O=4.65 ppm) δ: 0.8–1.1 (4H, m), 3.07 (1H, d, J=12.2 Hz), 3.47–3.63 (3H, m), 3.90 (1H, dd, J=7.3 and 13.9 Hz), 4.19 (2H, s). IR (KBr) cm$^{-1}$: 2928, 2832, 1628, 1574, 1396, 1306, 1128, 610. Elemental analysis for C$_{10}$H$_{18}$N$_2$O$_6$.H$_2$O: Calcd.(%); C, 42,85; H, 7.19; N, 9.99 Found (%); C, 42.95; H, 7.08; N, 9.87.

Optical purity of the thus obtained (S)-7-amino-5-azaspiro[2.4]heptane was measured in the following manner. A 18 mg portion of each of the thus obtained crystalline compound and its racemic body was dissolved in 1 ml of tetrahydrofuran and mixed with 50 mg of 3,5-dinitrobenzoyl chloride. A 0.006 ml of triethylamine was added dropwise to the mixture while cooling in an ice bath which was subsequently stirred at room temperature for 30 minutes. The solution was mixed with saturated sodium bicarbonate aqueous solution and chloroform to effect phase separation, and the resulting chloroform layer was analyzed by a high performance liquid chromatography (HPLC).
(HPLC conditions)
Column; SUMICHIRAL OA-4600 (4.6 mmø×250 mm).
Mobile phase; hexane:1,2-dichloroethane:ethanol=60:40:5.
Flow rate; 1.0 ml/min.
Detector; ultraviolet absorption detector (254 nm).
Retention time; (S)-form: 6.8 minutes, (R)-form: 10.0 minutes.
Analytical results of the crystals:
6.8 minutes (97%, (S)-form)
10.0 minutes (3%, (R)-form).

INVENTIVE EXAMPLE 10

1-C(RS)-1-Cyano-[(S)-1-phenylethylaminolmethyl]-1-ethoxycarbonylcycilopropane (Method 1)
An eggplant type flask was charged with 134 mg of potassium cyanide, 606 mg of (S)-1-phenylethylamine and 1 ml of water. After adding 142 mg of ethyl 1-formylcyclopropane-1-carboxylate dissolved in 2 ml of ethanol, dropwise at room temperature, the resulting mixture was further mixed with 0.2 ml of concentrated hydrochloric acid and stirred for 3 hours at the same temperature and then for 2.5 hours at 50° C. After confirming completion of the reaction, the reaction solution was mixed with ice water and extracted with ethyl acetate. Next, the resulting organic layer was washed with water and saturated brine, and dried over anhydrous magnesium sulfate and, after removing insoluble matter by filtration, the solvent was evaporated under a reduced pressure. Thereafter, the resulting residue was subjected to a silica gel column chromatography (hexane:ethyl acetate=10:1) to obtain 245 mg (87%) of a diastereomer mixture in the form of colorless oil.

(Method 2)
An eggplant type flask was charged with 10 g of ethyl 1-formylcyclopropane-1-carboxylate to which were further added 12.8 g of (S)-1-phenylethylamine dissolved in 100 ml of ethanol, 6.9 g of potassium cyanide dissolved in 40 ml of water and 22 g of sodium hydrogen sulfite in that order at 0° C. The reaction system was stirred for 2 hours at 50° C. After confirming completion of the reaction, the reaction solution was mixed with ice water and extracted with ethyl acetate. Next, the resulting organic layer was washed with water and saturated brine, and dried over anhydrous magnesium sulfate and, after removing insoluble matter by filtration, the solvent was evaporated under a reduced pressure. Thereafter, the resulting residue was subjected to a silica gel column chromatography (hexane:ethyl acetate=8:1) to obtain 15.7 g (82%) of a diastereomer mixture in the form of colorless oil. Formation ratio of the two diastereomers was calculated under the following analytical conditions. Further, these diastereomers were able to be separated by a thin layer chromatography (hexane:ethyl acetate=4:1).
(HPLC conditions)
Column; CHIRALCEL OJ (4.6 mmø×250 mm).
Mobile phase; hexane:1,2-dichloroethane:ethanol:methanol=500:10:1:1.
Flow rate; 1.0 ml/min.
Detector; ultraviolet absorption detector (254 nm).
Retention time; diastereomer A ((S)-(S) form):
17 minutes (73%)
diastereomer B ((R)-(S) form):
23 minutes (27%).
Diastereomer A
$^1$H-NMR (CDCl$_3$) δ: 0.80–0.89 (2H, m), 1.28 (3H, t, J=7.3 Hz), 1.2–1.4 (2H, m), 1.40 (3H, d, J=6.6 Hz), 2.66 (1H, s), 4.06 (1H, q, J=6.6 Hz), 4.20 (2H, q, J=7.3 Hz), 7.23–7.37 (5H, m). IR (KBr) cm$^{-1}$: 2980, 1722, 1182, 702. MS (m/z): 273, 246, 142, 105.
Diastereomer B
$^1$H-NMR (CDCl$_3$) δ: 0.92–1.06 (2H, m), 1.26 (3H, t, J=7.3 Hz), 1.34 (3H, d, J=6.6 Hz), 1.38–1.42 (2H, m), 3.41 (1H, s), 4.03 (1H, q, J=6.6 Hz), 4.19 (2H, q, J=7.3 Hz), 7.24–7.38 (5H, m). IR (KBr) cm$^{-1}$: 2980, 1724, 1182, 702. MS (m/z): 273, 246, 142, 105.

INVENTIVE EXAMPLE 11

1-f(RS)-1-Cyano-[(S)-1-(1-naphthyl) ethylaminolmethyl]-1-ethoxycarbonylcyclopropane An eggplant type flask was charged with 426 mg of ethyl 1-formylcyclopropane-1-carboxylate to which were further added 771 mg of (S)-1-(1-naphthyl)ethylamine dissolved in 5 ml of ethanol, 293 mg of potassium cyanide dissolved in 2 ml of water and-937 mg of sodium hydrogen sulfite in that order at 0° C. The reaction system was stirred for 3.5 hours at 50° C. After confirming completion of the reaction, the reaction solution was mixed with ice water and extracted with ethyl acetate. Next, the resulting organic layer was washed with water and saturated brine, and dried over anhydrous magnesium sulfate and, after removing insoluble matter by filtration, the solvent was evaporated under a reduced pressure. Thereafter, the resulting residue was subjected to a silica gel column chromatography (hexane:ethyl acetate=5:1) to obtain 698 mg (72%) of a diastereomer mixture in the form of colorless oil. Formation ratio of the two diastereomers was calculated under the following analytical conditions.
(HPLC conditions)
Column; CHIRALCEL OJ (4.6 mmø×250 mm).
Mobile phase; hexane:1,2-dichloroethane:ethanol= 500:10:2.
Flow rate; 1.0 ml/min.
Detector; ultraviolet absorption detector (254 nm).
Retention time; diastereomer A: 31 minutes (72%)
diastereomer B: 40 minutes (28%).
$^1$H-NMR (CDCl$_3$) δ: 0.73–0.97 (2H, m), 1.23 (3H×¼, t, J=7.3 Hz), 1.29 (3H×¾, t, J=7.3 Hz), 1.34–1.41 (2H, m), 1.51 (3H×¼, d, J=6.3 Hz), 1.56 (3H×¾, d, J=6.6 Hz), 2.75 (1H×¾, s), 3.53 (1H×¼, s), 4.08–4.28 (2H, m), 4.87–4.92 (1H, brq), 7.42–8.38 (7H, m).

INVENTIVE EXAMPLE 12

1-[(RS)-1-Cyano-[(S)-1-phenvlproiylamino]methyl]-1-ethoxycarbonylcyclopropane

An eggplant type flask was charged with 136 mg of potassium cyanide, 501 mg of (S)-1-phenylpropylamine and 1 ml of water. After adding 152 mg of ethyl 1-formylcyclopropane-1-carboxylate dissolved in 2 ml of ethanol, dropwise at room temperature, the resulting mixture was further mixed with 0.2 ml of concentrated hydrochloric acid, and stirred for 1 hour at the same temperature and then for 2 hours at 50° C. After confirming completion of the reaction, the reaction solution was mixed with ice water and extracted with ethyl acetate. Next, the resulting organic layer was washed with water and saturated brine, and dried over anhydrous magnesium sulfate and, after removing insoluble matter by filtration, the solvent was evaporated under a reduced pressure. Thereafter, the resulting residue was subjected to a silica gel column chromatography (hexane:ethyl acetate=10:1) to obtain 181 mg (59%) of a diastereomer mixture in the form of colorless oil. Formation ratio of the two diastereomers was calculated under the following analytical conditions.
(HPLC conditions)
Column; CHIRALCEL OJ (4.6 mmø×250 mm).
Mobile phase; hexane:1,2-dichloroethane:ethanol= 500:10:2.
Flow rate; 1.0 ml/min.
Detector; ultraviolet absorption detector (254 nm).
Retention time; diastereomer A: 12 minutes (72%)
diastereomer B: 16 minutes (28%).
Diastereomer A
$^1$H-NMR (CDCl$_3$) δ: 0.74–0.83 (2H, m), 0.87 (3H, t, J=7.3 Hz), 1.28 (3H, t, J=7.3 Hz), 1.34–1.41 (2H, m), 1.70 (2H, m), 2.63 (1H, s), 3.77 (1H, t, J=6.9 Hz), 4.21 (2H, q, J=7.3 Hz), 7.23–7.36 (5H, m).

INVENTIVE EXAMPLE 13

1-((RS)-1-Cyano-[(S)-1-phenyl-2-p-tolylethylamino]methyll-1-ethoxycarbonylcyclopropane An eggplant type flask was charged with 133 mg of potassium cyanide, 1.0 g of (S)-1-phenyl-2-p-tolylethylamine and 1 ml of water. After adding 146 mg of ethyl 1-formylcyclopropane-1-carboxylate dissolved in 2.5 ml of ethanol, dropwise at room temperature, the resulting mixture was further mixed with 0.2 ml of concentrated hydrochloric acid, and stirred for 1 hour at the same temperature and then for 2 hours at 50° C. After confirming completion of the reaction, the reaction solution was mixed with ice water and extracted with ethyl acetate. Next, the resulting organic layer was washed with water and saturated brine, and dried over anhydrous magnesium sulfate and, after removing insoluble matter by filtration, the solvent was evaporated under a reduced pressure. Thereafter, the resulting residue was subjected to a silica gel column chromatography (hexane:ethyl acetate=10:1) to obtain 251 mg (67%) of a diastereomer mixture in the form of colorless oil. Formation ratio of the two diastereomers was found to be 4:1 based on the integral ratio of NMR.
$^1$H-NMR (CDCl$_3$) δ: 0.62–0.88 (2H, m), 1.04 (3H×⅘, t, J=7.3 Hz), 1.11 (3H×⅕, t, J=7.3 Hz), 1.25–1.45 (2H, m), 2.30 (3H×⅕, s), 2.32 (3H×⅘, s), 2.64 (1H×⅘, s), 2.73–3.03 (2H, m), 3.06 (1H×⅕, s), 3.78–4.23 (3H, m), 7.03–7.40 (9H, m).

INVENTIVE EXAMPLE 14

Epimerization of 1-[(R)-1-cyano-F(S)-1-phenylethylaminolmethyl]-1-ethoxycarbonylcyclopropane A 10 mg portion of 1-[(R)-1-cyano-[(S)-1-phenylethylamino]methyl]–1-ethoxycarbonylcyclopropane obtained in Inventive Example 10 was mixed with 1 ml of ethanol and heated under reflux for 30 minutes. After completion of the reaction, the reaction solution was concentrated under a reduced pressure to obtain a diastereomer mixture of 1-[(S)-1-cyano-[(S)-1-phenylethylamino]methyl]-1-ethoxycarbonylcyclopropane and 1-[(R)-1-cyano-[(S)-1-phenylethylamino]methyl]-1-ethoxycarbonylcyclopropane (formation ratio; 72:28).
(HPLC conditions)
Column; CHIRALCEL OJ (4.6 mmø×250 mm).
Mobile phase; hexane:1,2-dichloroethane:ethanol:methanol=500:10:1:1.
Flow rate; 1.0 ml/min.
Detector; ultraviolet absorption detector (254 nm).
Retention time; diastereomer A ((S)-(S) form): 17 minutes (before the reaction: 0%, after the reaction: 73%)
diastereomer B ((R)-(S) form): 23 minutes (before the reaction: 100%, after the reaction: 27%).

INVENTIVE EXAMPLE 15

(s)-7-F (S)-1-Phenylethyliamino-4-oxo-5-azaspiro[2.4]heptane

An autoclave was charged with 1.0 g of 1-[(S)-1-cyano-[(S)-1-phenylethylamino]methyl]-1-ethoxycarbonylcyclopropane, 1.7 ml of Raney nickel and 17 ml of ammonia-saturated ethanol, and the contents were stirred at room temperature for 1.5 hours in an atmosphere of hydrogen under a pressure of 35 kg/cm$^2$. After completion of the reaction, the catalyst was removed by filtration and the resulting filtrate was concentrated under a reduced pressure. The resulting residue was dissolved in 20 ml of ethanol, put into an autoclave and heated at 180° C. for 8.5 hours. After completion of the reaction, the solvent was evaporated under a reduced pressure, and the resulting residue was mixed with isopropanol and stirred to obtain 621 mg (74%) of the title compound in the form of slightly yellow crystals. The thus obtained compound was recrystallized from ethanol and isopropanol, and used as a sample for analyses.

Melting point: 126.5–127.5° C. $^1$H-NMR (CDCl$_3$) δ: 0.58–0.66 (1H, m), 0.89–1.01 (1H, m), 1.05–1.11 (2H, m), 1.32 (3H, d, J=6.6 Hz), 3.14 (1H, dd, J=4.6 and 6.9 Hz), 3.24 (1H, dd, J=4.6 and 9.2 Hz), 3.63 (1H, dd, J=6.9 and 9.2 Hz), 3.84 (1H, q, J=6.6 Hz), 5.45 (1H, brs), 7.21–7.34 (5H, m).

The same reaction was carried out using the diastereomer mixture obtained in Inventive Example 10. Analytical data of the thus formed product are as follows.

Melting point: 107–110.5° C. $^1$H-NMR (CDCl$_3$) δ: 0.58–1.25 (4H, m), 1.315 (1H×27/100, d, J=6.6 Hz), 1.322 (1H×73/100, d, J=6.6 Hz), 2.91 (1H×27/100, dd, J=5.3 and 9.2 Hz), 3.14 (1H×73/100, dd, J=4.6 and 6.9 Hz), 3.24 (1H×73/100, dd, J=4.6 and 9.2 Hz), 3.36 (1H×27/100, dd, J=7.3 and 9.2 Hz), 3.44 (1H×27/100, dd, J=5.3 and 7.3 Hz), 3.63 (1H, dd, J=6.9 and 9.2 Hz), 3.75 (1H×27/100, q, J=6.6 Hz), 3.84 (1H×73/100, q, J=6.6 Hz), 7.21–7.34 (5H, m).

INVENTIVE EXAMPLE 16

(S)-7-[(S)-1-Phenylethyl]amino-5-azaspiro[2.4]heltane

A flask was charged with 200 mg of (S)-7-[(S)-1-phenylethyl]amino-4-oxo-5-azaspiro[2.4]heptane, and the atmosphere in the flask was replaced with nitrogen. Next, 5 ml of tetrahydrofuran was added to dissolve the compound in the flask, 5.0 ml of lithium aluminum hydride (1 M solution in tetrahydrofuran) was added dropwise to the resulting solution at 0° C. and then the mixture was heated under reflux for 1 hour. After confirming completion of the reaction, the reaction was terminated by adding saturated ammonium chloride solution and then the insoluble matter was removed by filtration. The resulting filtrate was concentrated under a reduced pressure and distributed between ethyl acetate and saturated brine, and the resulting organic layer was dried over anhydrous sodium sulfate. Thereafter, the insoluble matter was removed by filtration and the resulting filtrate was concentrated under a reduced pressure to obtain 181 mg (96%) of colorless oily substance.

$^1$H-NMR (CDCl$_3$) δ: 0.41–0.50 (3H, m), 0.68–0.80 (1H, m), 1.32 (3H, d, J=6.6 Hz), 2.47 (1H, dd, J=3.3 and 5.0 Hz), 2.68 (1H, d, J=10.9 Hz), 2.93 (1H, dd, J=3.3 and 11.2 Hz), 3.07 (1H, d, J=10.9 Hz), 3.10 (1H, dd, J=5.0 and 11.2 Hz), 3.74 (1H, q, J=6.6 Hz), 7.19–7.35 (5H, m).

INVENTIVE EXAMPLE 17

(S)-7-Amino-5-azaspiro[2.4]heptane dihydrochloride

An autoclave was charged with 79 mg of (S)-7-[(S)-1-phenylethyl]amino-5-azaspiro[2.4]heptane, 37 mg of 20% palladium hydroxide, 2 ml of ethanol, 1 ml of water and 0.5 ml of concentrated hydrochloric acid, and the contents were stirred overnight at room temperature in an atmosphere of hydrogen (40 kgf/cm$^2$). After completion of the reaction, the catalyst was removed by filtration and the resulting filtrate was concentrated under a reduced pressure to obtain 72 mg (82%) of the title compound in the form of colorless crystals. The thus obtained crystal compound was recrystallized from ethanol and diethyl ether and used as a sample for analyses.

Melting point: 240–248° C. (decomposition). $^1$H-NMR (D$_2$O, H$_2$O=4.65 ppm) δ: 0.86–1.16 (4H, m), 3.16 (1H, d, J=12.2 Hz), 3.59 (1H, dd, J=3.3 and 13.9 Hz), 3.63 (1H, d, J=12.2 Hz), 3.73 (1H, dd, J=3.3 and 7.6 Hz), 4.01 (1H, dd, J=7.6 and 13.9 Hz).

Optical purity of the thus obtained (S)-7-amino-5-azaspiro[2.4]heptane was measured in the following manner.

A 18 mg portion of each of the thus obtained crystalline compound and its racemic body was dissolved in 1 ml of tetrahydrofuran and mixed with 50 mg of 3,5-dinitrobenzoyl chloride. A 0.06 ml of triethylamine was added dropwise to the mixture while cooling in an ice bath which was subsequently stirred at room temperature for 30 minutes. The solution was mixed with saturated sodium bicarbonate aqueous solution and chloroform to effect phase separation, and the resulting chloroform layer was analyzed by a high performance liquid chromatography (HPLC).

(HPLC conditions)
Column; SUMICHIRAL OA-4600 (4.6 mmø×250 mm).
Mobile phase; hexane:1,2-dichloroethane:ethanol=60:40:5.
Flow rate; 1.0 ml/min.
Detector; ultraviolet absorption detector (254 nm).
Retention time; (S)-form: 6.8 minutes, (R)-form: 10.0 minutes.
Analytical results of the crystals:
 6.8 minutes (>99%, (S)-form)
 10.0 minutes (<1%, (R)-form).

INDUSTRIAL APPLICABILITY

The present invention is to provide a novel material compound (represented by formula (I)) to be used in the production of a quinolone derivative which is expected as an excellent antibacterial agent and a novel method for the synthesis thereof, and to provide a process for the inexpensive, short-step and industrially advantageous production of nitrogen-containing heterocyclic compounds having a spiro-cyclic structure which are obtained from the compound represented by formula (I), particularly an optically active azaspiro[2.4]heptane derivative.

What is claimed is:

1. A compound represented by formula (III):

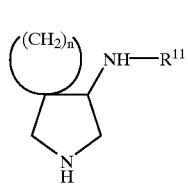

(III)

wherein n is an integer of 2 to 5; and

R$^{11}$ represents a substituent group represented by formula:

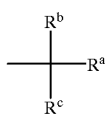

wherein

R$^a$, R$^b$ and R$^c$ each represents a phenyl, phenylmethyl or naphthyl group (which may be substituted with at least one substituent group selected from the group consisting of an alkyl group having 1 to 4 carbon atoms, an alkoxyl group having 1 to 4 carbon atoms, a halogen atom and a nitro group), a hydrogen atom, or an alkyl group having 1 to 4 carbon atoms, with the proviso that R$^a$, R$^b$ and R$^c$ are different from one another, and a salt thereof.

2. The compound or a salt thereof according to claim 1, which has the following configuration,

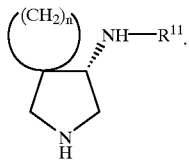

* * * * *